United States Patent
Kleen et al.

(10) Patent No.: US 7,406,346 B2
(45) Date of Patent: *Jul. 29, 2008

(54) OPTICAL COHERENCE TOMOGRAPHY SYSTEM FOR THE EXAMINATION OF HUMAN OR ANIMAL TISSUE OR ORGANS

(75) Inventors: Martin Kleen, Neunkirchen (DE); Norbert Rahn, Forchheim (DE)

(73) Assignee: Siemens Aktiengesellschaft, Munich (DE)

(*) Notice: Subject to any disclaimer, the term of this patent is extended or adjusted under 35 U.S.C. 154(b) by 648 days.

This patent is subject to a terminal disclaimer.

(21) Appl. No.: 10/851,936

(22) Filed: May 21, 2004

(65) Prior Publication Data

US 2005/0020925 A1    Jan. 27, 2005

(30) Foreign Application Priority Data

May 22, 2003  (DE) ............... 103 23 217

(51) Int. Cl.
*A61B 5/05* (2006.01)
(52) U.S. Cl. ............... 600/424; 600/476
(58) Field of Classification Search ........... 600/424, 600/476
See application file for complete search history.

(56) References Cited

U.S. PATENT DOCUMENTS

| 5,752,518 | A | * | 5/1998 | McGee et al. ............ 600/424 |
| 5,795,295 | A | * | 8/1998 | Hellmuth et al. ......... 600/407 |
| 5,830,145 | A | * | 11/1998 | Tenhoff .................. 600/463 |
| 6,175,669 | B1 | * | 1/2001 | Colston et al. ........... 385/12 |
| 2002/0049375 | A1 | * | 4/2002 | Strommer et al. ......... 600/407 |
| 2002/0077546 | A1 | | 6/2002 | Aldefeld et al. | |

FOREIGN PATENT DOCUMENTS

EP    0 961 125    12/1999

OTHER PUBLICATIONS

Three-Dimensional Reconstruction of In Vivo Blood Vessels in Human Skin Using Phase-Resolved Optical Doppler Tomography, Zhao et al., IEEE J. on Selected Topics in Quantum Electronics, vol. 7, No. 6 (Nov./Dec. 2001) pp. 931-935.

* cited by examiner

*Primary Examiner*—Ruth S. Smith
*Assistant Examiner*—Jonathan G Cwern
(74) *Attorney, Agent, or Firm*—Schiff Hardin LLP

(57) ABSTRACT

In an optical coherence tomography system for the examination of human or animal tissue or organs, a catheter is insertable into the tissue or organ to introduce light into the tissue or organ and the reflection is transmitted to an evaluation unit, where the reflection and a reference light are evaluated interferometrically to determine a two-dimensional cross-sectional view of the tissue or organ. At least one position sensor is at the tip of the catheter, and a position-determining system derives position data describing the current position of the position sensor in the coordinate system of the position-determining system. The position-determining system also captures position data regarding the spatial position of the cross-sectional views in the same coordinate system and the evaluation system derives a three-dimensional view from several of the cross-sectional views and the corresponding position data.

9 Claims, 3 Drawing Sheets

OPTICAL COHERENCE TOMOGRAPHY SYSTEM FOR THE EXAMINATION OF HUMAN OR ANIMAL TISSUE OR ORGANS

BACKGROUND OF THE INVENTION

1. Field of the Invention

The present invention proposes an optical coherence tomography system for the examination of human or animal tissue or organs of the type including a catheter that is insertable into the tissue or organ, by which light is introduced into the tissue or organ and the reflection is transmitted to an evaluation unit, where the reflection and a reference light are evaluated interferometrically to generate a two-dimensional cross-sectional view of the tissue or organ, wherein the evaluation unit uses several two-dimensional cross-sectional views to derive a three-dimensional view of the tissue or organ, and wherein at least one position sensor is disposed on or in the tip of the catheter, as part of a position-determining system for deriving position data describing the current position of the position sensor in the coordinate system of the position-determining system.

2. Description of the Prior Art

Optical coherence tomography (OCT) is a medical examination modality, in which two-dimensional cross-sectional views of the object to be examined are obtained by shining light via a catheter into the object and then analyzing the reflection. In a method similar to B-mode ultrasound, light is emitted and the tissue or organ reflection is analyzed to derive information about the structure of the illuminated object. The depth information, i.e. the visual information about the tissue or organ, is derived in coherence tomography by means of interferometry with a reference light source of known length. The length of the reference light source is modified constantly. The interference at the interferometer corresponds to object points in the examination light ray, for which the reference ray and the examination light ray measured to the object point in question are of equal length. Light is introduced into the tissue by means of a thin catheter with a diameter of 1 mm or less. Consequently, optical coherence tomography may be used wherever a catheter may be inserted. Examples include, but are not restricted to, views of the inner surface and outer surface of vessels, the gastrointestinal tract, the urogenital tract, the eyes or the skin.

Optical coherence tomography yields two-dimensional cross-sectional views from scanning by means of the light ray emitted from the catheter, which rotates to generate a local cross-sectional view. Thus, it is a ring or annular view with a rotating light ray, primarily a laser. The doctor sees a two-dimensional cross-sectional view of the just-scanned area in real time. A method is known to derive a three-dimensional view of the vessel or organ from a number of two-dimensional cross-sectional views and to display it on a monitor in order to give the doctor a three-dimensional view of the vessel or organ for better diagnostic evaluation. Thus the doctor can see a three-dimensional view of the examined organ based on the many two-dimensional cross-sectional views. The three-dimensional view simplifies the estimation of the three-dimensional extent of anatomical structures and any pathological processes that are present.

A disadvantage of known coherence tomography systems is the lack of information regarding the relative position of the individual cross-sectional views, as the derivation of the three-dimensional view treats the cross-sectional views as parallel to each other. Consequently, the vessel, which is coiled and non-linear, is shown as a linear three-dimensional unit. The doctor will in fact see a three-dimentional view, but that view does not show the true three-dimensional extent and the path of the vessel or organ being examined, thus also not the length, width and actual location of any pathological structures present. As a result, the three-dimensional views impose limits on the quality of the final diagnosis.

German OS 100 51 244 discloses a mechanism for determining the position of a medical instrument introduced into the object being examined, as well as to view the vicinity of the medical instrument, such as a catheter, by means of a position sensor located in the tip of the instrument in conjunction with a position-determining system. A three-dimensional overview of the area where the position sensor is currently located, as indicated by the position sensor, is computed based on a set of three-dimensional view data collected prior to the intervention itself. This three-dimensional overview is transmitted to a monitor. The current position of the position sensor is indicated in this three-dimensional overview. In addition to this three-dimensional overview, the current two-dimensional view taken by the OCT scanner, which is built into the instrument, is also displayed on the monitor.

An article by Y. Zhao et al entitled Three-Dimensional Reconstruction of in Vivo Blood Vessels in Human Skin Using Phase-Resolved Optical Doppler Tomography, IEEE Journal on Selected Topics in Quantum Electronics, Vol. 7, No. 6, pages 931-935, 2001, describes a three-dimensional reconstruction procedure on the basis of optical Doppler tomography views.

SUMMARY OF THE INVENTION

An object of the present invention is to provide an optical coherence tomography system that is an improvement over the current state of the art.

This object is achieved in accordance with the invention by an optical coherence tomography system of the type initially described above, but which enables the position-determining system to capture the position data for the location of the cross-sectional views in the coordinate system of the position-determining system and wherein the evaluation system is programmed to derive the three-dimensional view on the basis of the cross-sectional views and the corresponding position data.

The use of the position sensor in accordance with the invention allows the position-determining system to collect information regarding the position and orientation of the coherence tomography catheter as well as position information as to the location of the cross-sectional views. It is thus possible to collect position data and to match position data to each two-dimensional cross-sectional view that has been taken or will be taken. This means that the position and orientation of each completed cross-sectional view in the coordinate system of the position-determining system is known. That also identifies the relative position of any two cross-sectional views, so a three-dimensional view on the basis of the spatial information for the individual cross-sectional views can be generated, where the examined space is shown in its true geometry and size. Consequently, the doctor can see a three-dimensional view on a suitable monitor, which shows the object being examined (either after the examination is completed or even while the examination is still in progress based on the cross-sectional views obtained to that point) in its true size, such that the doctor can note the true three-dimensional extent of the anatomical structures or of any pathological processes present. For example, this makes it feasible to display three-dimensional views of vessel pathology (such as "vulnerable plaque" or pathological changes in hollow organs, such as scar tissue formed in the heart after infarcts), to identify and to quantify the same, where the depicted space corresponds to the actual interior situation. The doctor thus gains a substantial benefit in the diagnostic reliability of the depicted space and an improvement of the optical coherence tomography procedure in a diagnostic sense.

Known optical coherence tomography systems often use a time delay between cross-sectional views, i.e. a cross-sectional view is obtained after the end of a specified time interval. This leads to a large amount of data, since cross-sectional views are obtained even though the catheter may not have moved at all. An alternative is known with the movement of the catheter being controlled by a control motor, where a suitable mechanism is linked to the catheter with a step motor to control movement such that the catheter is moved by steps of a fixed increment. Such systems generally obtain a view after the catheter comes to rest in a new position after each movement. A disadvantage of this procedure is the need to use additional movement mechanisms. Moreover, the doctor generally has no possibility of guiding the catheter manually in order to view certain spaces longer or again.

In order to overcome such disadvantages in an embodiment of the invention a trigger is emitted from the position-determining system to the control unit to obtain a cross-sectional view, or to trigger the evaluation system to generate a three-dimensional view, only when the relevant position data indicate movement of the catheter by a specified spatial increment.

In this embodiment of the invention the coherence tomography system is triggered only on the basis of data provided by the position-determining system. A cross-sectional view generally will be obtained only when the position-determining system indicates movement of the catheter by a specified spatial increment. In contrast to conventional systems, the inventive system has no need for a mechanical device, such as a stepper motor or the like. Instead the doctor can move the catheter manually as desired, and the movement is measured (detected) with precision by the position-determining system in order to control the production of views. At the same time, this overcomes the problems of control solely by time-intervals.

As an alternative to control the view-obtaining process on the basis of information supplied by the position-determining system, there is an option to allow the view-obtaining process to operate independently, such as on a fixed time interval, and to display all obtained cross-sectional views on a continuous basis on the monitor. The position data are used only when the computation to derive the three-dimensional view is started, i.e. the evaluation unit uses only those cross-sectional views that are separated by movement of the catheter by a specified spatial increment to derive the three-dimensional view. This method minimizes the data required for the derivation of the three-dimensional view, while allowing for cross-sectional views to be obtained and displayed continuously. In any case, the doctor has complete freedom regarding the movement of the catheter. He or she can stop the catheter at any time or even reverse its movement, since the position-determining system will unambiguously recognize the status on the basis of the detected information regarding the incremental movement. Even if the movement of the catheter is reversed, this does not cause additional views showing a previously examined section to enter into the derivation of the three-dimensional view, because the computation can be restricted to those views separated by movement of the catheter of a specified increment in one direction only, such as from interior to exterior, or anterior or posterior.

In order to spatially specify the position and spatial orientation of the position sensor, and thus also the position of the tip of the catheter and the associated cross-sectional views in the coordinate system of the position-determining system, as precisely as possible, it is useful to have the position-determining system define the position of the position sensor by the position data for six variables, with the specified spatial increment defining movement along at least one variable. Thus each position is defined by six bits of position data, which describe the position along the x, y, and z-axes of the coordinate system of the position-determining system, as well as the applicable rotation or twist around one of these axes as the other three bits of position data. The spatial increment is then defined as movement in at least one direction. In other words, if the catheter is moved precisely along one of the axes of the coordinate system, such movement is described in a single direction, which may serve as the trigger, if the movement is sufficiently large. Any other movement involves movement in two or more directions, which in conjunction also may be compared to the specified spatial increment required as a trigger.

In a further embodiment of the invention the control unit or the evaluation unit of the unit that monitors the movement of the tissue or organ can be triggered in such a manner that cross-sectional views are obtained only in the presence of certain organ conditions, or only cross-sectional views of certain organ conditions are processed. This embodiment of the invention has an additional external trigger, in addition to the trigger in the position-determining unit, which makes it possible to obtain or derive a three-dimensional view of specific conditions of the vessel or organ by taking two-dimensional cross-sectional views only in this phase or by processing for the 3D derivation only those cross-sectional views, which were obtained in this phase. For example, it is possible to employ a trigger on the basis of an ECG or a trigger based on breathing movements. In this example, it is possible to obtain cross-sectional views only in a particular phase of the respiratory cycle or in a particular heart cycle phase or to use only those cross-sectional views that were obtained in a particular respiratory or heart cycle phase to derive the three-dimensional view.

It is also possible for the evaluation unit to be equipped to combine the two-dimensional cross-sectional views with other two-dimensional views that were obtained with a different examination modality, with the views superimposed by reference to corresponding pairs of anatomical landmarks common to both views. If the corresponding pairs of anatomical landmarks are identified in the morphological data set obtained by such a different examination process (such as data obtained by CT, MR, ultrasound etc.) and also by the position-determining system of the position sensor of the catheter in the OCT view in this embodiment of the invention, then the position and orientation of the catheter can be visualized in the morphological data derived from the different examination modality and the two-dimensional coherence tomography cross-sectional views can be combined with the morphological data. Thus, there is the possibility to superimpose a two-dimensional coherence tomography cross-sectional view onto a view taken with a different examination modality with precise alignment in position and orientation, with the determination of the spatial orientation of the coherence tomography cross-sectional view relative to the cross-sectional view of the other examination modality being based on anatomical landmarks.

A further embodiment of the invention combines the three-dimensional view derived by the evaluation unit with an additional three-dimensional view obtained from a different examination modality, with both three-dimensional views having known positions in the coordinate system of the position-determining system. This embodiment of the invention combines a three-dimensional morphological data set, which may have been derived from 3D-angiography or 3D-ultrasound, with the three-dimentional view data derived from optical coherence tomography. If the positions of both data sets in the coordinate system of the position-determining system are known (i.e. if both used a position-determining system), then both 3D view data sets can be matched without a "marker", which means that there is no need to match two different coordinate systems when both views are based on the same coordinate system. This method allows the OCT three-dimensional view to be merged easily with respect to position and orientation with a 3D angiography view, for example, which gives the doctor additional information about the vicinity of the tissue or organ examined by coherence tomography.

In addition to the optical coherence tomography system, the invention also concerns a catheter for such an optical coherence tomography system, which shines light into tissue or organs and transmits the reflected light to an evaluation system, the catheter having at least one position sensor at (i.e., on or in) its tip, with the spatial position of the sensor being tracked in the coordinate system of a position-determining system, and with the position of the sensor being described by observations for six variables.

DESCRIPTION OF THE PREFERRED EMBODIMENTS

Figure 1:
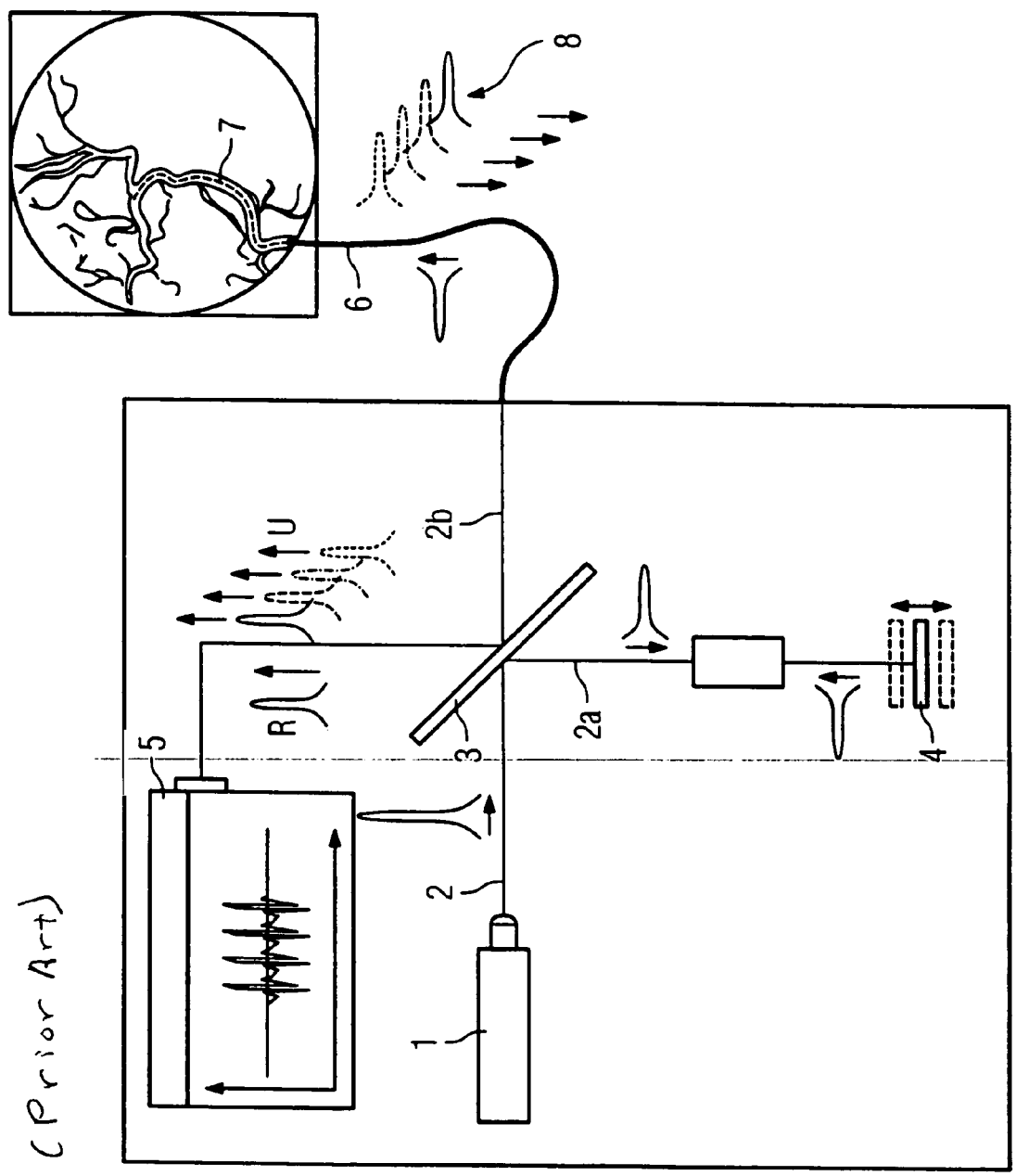
FIG. 1 is for use in explaining the fundamentals of optical coherence tomography.

FIG. 1 explains the basic concept of optical coherence tomography. A light source, a laser 1 in the present example, emits a ray of light 2 toward a semi-transparent mirror 3. A first part 2a of the light ray is deflected to a reference branch, where the length of ray 2a is modulated by means of a movable mirror 4, for example. The modulated reflected light strikes the semi-transparent mirror 3 and continues as reference light component R toward an interferometer 5.

A second part 2b of the light ray enters a catheter 6, which is inserted into a vessel 7 in this example. The light is emitted from the tip of catheter 6 and shines on the tissue of the vessel 7. The reflected light, which is also modulated depending on the position of the reflecting surface as indicated by the four reflection light symbols 8, again enters the catheter 6, continues to the semi-transparent mirror 3 and from there continues as a reflected examination light component U to the interferometer 5. The interferometer 5 processes the two light components R and U and determines their coherence. The OCT procedure is essentially known and does not need further detailed explanation.

Figure 2:
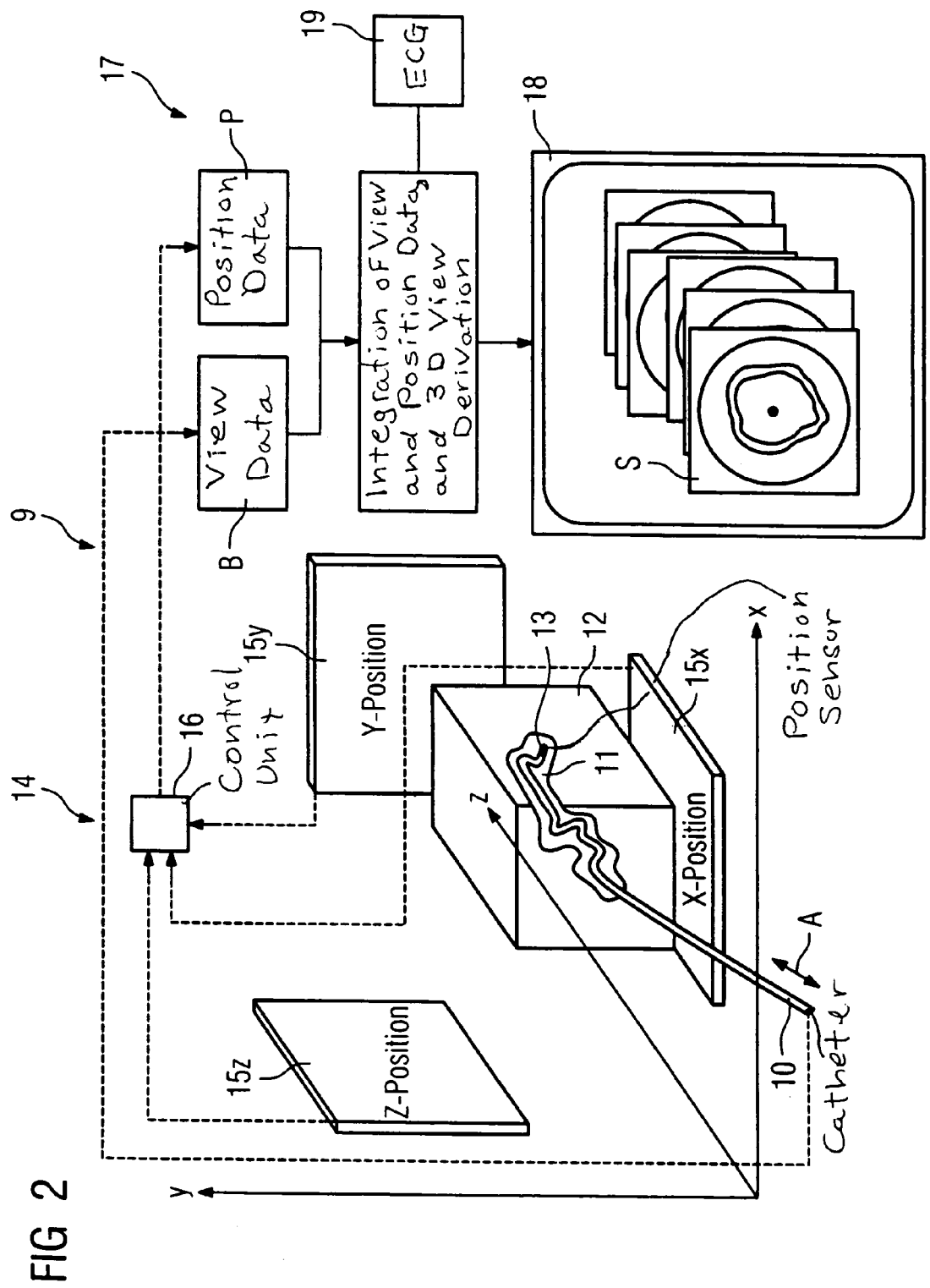
FIG. 2 schematically illustrates an embodiment of the coherence tomography system of the invention.

FIG. 2 shows the optical coherence tomography system 9 of the invention. This includes the previously described catheter 10, which the doctor in this example has inserted manually in vessel 11 of the object 12 to be examined. At the tip of the catheter 10, a position sensor 13 is disposed, which in this embodiment is an electromagnetic transmitter and is used to locate the position and orientation in the coordinate system, depicted here by coordinate axes x, y, and z, of position-determining system 14. In order to facilitate this, position-determining system 14 of the depicted example has three external reception coils 15x, 15y, and 15z, by which the current position of position sensor 13 is identified in the x, y, and z directions, as well as the respective rotation of the position sensor 13 around these axes. Thus, each sensor position is described by six bits of position data, namely x, y, and z, as well as the respective rotation around these axes.

A control unit 16 of the position-determining system 14 determines the current position data and transmits the data position data P to an evaluation unit 17.

As was already described in connection with FIG. 1, light is introduced into the tissue via catheter 10, which is connected to a light source that is not shown, and the light is reflected such that two-dimensional ring views in the form of two-dimensional cross-sectional views S are produced. To produce such cross-sectional views, the reflected light resulting from the light emissions is captured by the tip of the catheter 10 and is then transmitted via the catheter 10 and is combined with the reference light component (not shown in FIG. 2) and supplied to evaluation unit 17, where the information is evaluated by means of the interferometer already described in FIG. 1 to produce two-dimensional cross-sectional views or cross-sectional view data B that contain the view information.

As indicated by the double arrow A, the catheter can be moved relative to a vessel 11. Since each movement implies a change in the position of the position sensor 13, the position-determining system 14 can capture any change in position or orientation, no matter how small. It is advantageous to trigger the view obtaining or initiating the evaluation process by this information such that, for example, a two-dimensional cross-sectional view is obtained only if the position sensor 13 is moved by a specified increment (in one or at least one of the listed six variables), which can always be identified by the position-determining system 14. For example, this can preclude cross-sectional views from being unnecessarily continuously obtained, while the catheter is stationary, and from being processed subsequently to a three-dimentional reconstructed view (to be discussed below), which would lead to an excessive accumulation of data. It is also possible to use this information to select the cross-sectional views to be used in the derivation of the 3D view from the array of continuously generated cross-sectional views. The operating method may vary in this regard.

In any case, the evaluation unit 17, which has access to the view data B and the position data P, "marries" the two data sets, i.e. each two-dimensional cross-sectional view or set of view data is matched to the corresponding position data set. The evaluation unit 17 then derives the three-dimensional view from these position data and the view data. Since the position data for each cross-sectional view S are known and show how each cross-sectional view is positioned or oriented in relation to any other cross-sectional view, the 3D spatial view can be derived in a manner representing the actual geometric shape of vessel 11. This means that the three-dimensional representation displayed on monitor 18 represents the vessel 11 in its actual three-dimensional shape, which gives the doctor a view of the current interior situation. This feature, i.e. to array the individual cross-sectional views in their actual relationship to each other, is depicted in FIG. 2 by means of the offset of cross-sectional views S. It should be noted, however, that the cross-sectional views may, of course, be tilted relative to each other, depending on the actual shape of vessel 11.

FIG. 2 also depicts the use of an external trigger, here as a simultaneously procured ECG 19, to activate the process so as to use only those two-dimensional cross-sectional views or view data taken during the same phase to derive the three-dimensional view. This is particularly useful, if the vessel 11 is a coronary vessel or the like, so that the views are taken during the same heartbeats phase. In addition to this external trigger, which relates to view processing, it is also possible to combine this external trigger with the movement data supplied by the position-determining system 14. In that case, the views are obtained only if both conditions apply, namely that the incremental movement has been made and the appropriate trigger phase has been reached.

The coherence tomography system 9 of the invention thus allows views to be obtained in any orientation, with the position data being captured and linked, and then used to derive a three-dimensional view that represents the true conditions. This also allows the option of the evaluation unit 17 combining and displaying on the monitor those two-dimensional cross-sectional views with known position data, with unambiguous matching to two-dimensional coherence tomography cross-sectional views. For this purpose, anatomical landmarks identified in the various data sets can be used to match the coherence tomography cross-sectional views and the cross-sectional views derived from other modalities, so that the views can be combined. In addition, there is the option of the evaluation unit 17 combining the derived 3D view with another 3D view derived by some other modality and displaying the views simultaneously, particularly if both data sets were derived with the same coordinate system, namely with the position-determining unit 14, so the views can be matched easily.

Figure 3:
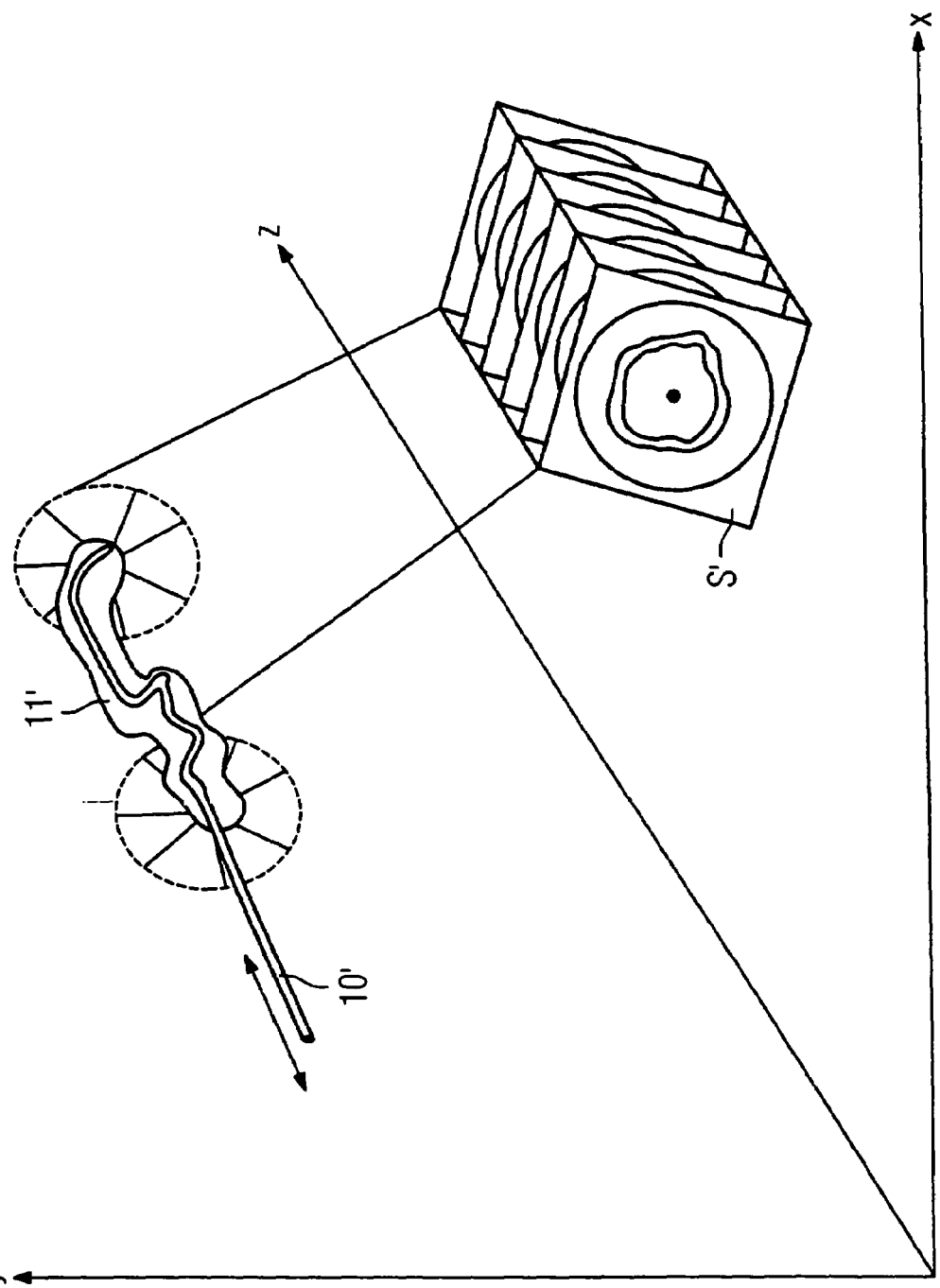
FIG. 3 schematically illustrates the 3D representation derived from two-dimensional coherence tomography cross-sectional views according to the current state of the art.

FIG. 3 illustrates the disadvantage of the current state of the art, where a conventional catheter 10' is used, which does not contain a position sensor. If this catheter is moved in a vessel 11', many cross-sectional views S' can be obtained, but these are processed without regard to their position or orientation data. Overall, as FIG. 3 depicts, a straight line space is generated by the derivation of the 3D view based on cross-sectional views S', which may have any angle or orientation towards each other, such that the 3D view does not reflect the actual geometric relationship of the vessel 11'. Thus, the doctor obtains an erroneous impression of the space being examined.

Although modifications and changes may be suggested by those skilled in the art, it is the intention of the inventors to embody within the patent warranted hereon all changes and modifications as reasonably and properly come within the scope of their contribution to the art.

We claim as our invention:

1. An optical coherence tomography system for examining human or animal tissue or organs comprising:
   a catheter adapted for insertion into a body of a subject;
   a light source connected to the catheter that directs light, via the catheter, onto a region in the body of the subject, said catheter detecting light reflected from said body region;
   an evaluation unit supplied with said reflected light and with reference light that evaluates the reflected light and the reference light interferometrically to determine a two-dimensional cross-sectional view of said region;
   a position sensor disposed at a tip of the catheter;
   a position determining system that interacts with said position sensor to derive position data describing a current position of the position sensor in a coordinate system and to derive further position data describing a spatial distribution of a plurality of cross-sectional views of said region obtained as said catheter is moved in said body, said position determining system triggering obtaining the respective cross-sectional views in said plurality of cross-sectional views only if said position data indicate movement of said catheter by a predetermined spatial increment; and
   said evaluation unit deriving a three-dimensional view of said region from said plurality of two-dimensional cross-sectional views using said position data and said further position data.

2. An optical coherence tomography system as claimed in claim 1 wherein said position data comprise six variables, and wherein said position determining system determines said predetermined spatial increment from at least one of said six variables.

3. An optical coherence tomography system as claimed in claim 1 wherein said evaluation unit is supplied with view data representing a two-dimensional view of said body region obtained with a different examination modality, and wherein said evaluation unit combines said two-dimensional cross-sectional views with said view represented by said view data by overlaying said two-dimensional cross-sectional views with said view represented by said view data based on anatomical landmarks that are present in each of said two-dimensional cross-sectional views and said view represented by said view data.

4. An optical coherence tomography system as claimed in claim 1 wherein said evaluation unit is supplied with view data representing a three-dimensional view of said region obtained by a different examination modality, referenced to said coordinate system, and wherein said evaluation unit combines said three-dimensional view derived from said plurality of two-dimensional cross-sectional views with said three-dimensional view represented by said view data by referencing both of said three-dimensional views to said coordinate system.

5. An optical coherence tomography system for examining human or animal tissue or organs comprising:
   a catheter adapted for insertion into a body of a subject;
   a light source connected to the catheter that directs light, via the catheter, onto a region in the body of the subject, said catheter detecting light reflected from said body region;
   an evaluation unit supplied with said reflected light and with reference light that evaluates the reflected light and the reference light interferometrically to determine a two-dimensional cross-sectional view of said region;
   a position sensor disposed at a tip of the catheter;
   a position determining system that interacts with said position sensor to derive position data describing a current position of the position sensor in a coordinate system and to derive further position data describing a spatial distribution of a plurality of cross-sectional views of said region obtained as said catheter is moved in said body;
   said evaluation unit deriving a three-dimensional view of said region from said plurality of two-dimensional cross-sectional views using said position data and said further position data; and
   said evaluation unit including a cross-sectional view in the derivation of said three-dimensional view only if said position data indicate movement of said catheter has occurred by a predetermined spatial increment for obtaining that cross-sectional view.

6. An optical coherence tomography system as claimed in claim 5 wherein said position data comprise six variables, and wherein said position determining system determines whether said predetermined spatial increment has occurred from at least one of said six variables, and provides an indication as to whether said movement by said predetermined spatial increment has occurred to said evaluation unit.

7. An optical coherence tomography system as claimed in claim 5 comprising a display in communication with said evaluation unit for displaying movement of said body region and wherein said evaluation unit triggers said display for displaying said movement only if a predetermined condition exists in said body region, in addition to movement of said catheter by said predetermined spatial increment.

8. An optical coherence tomography system as claimed in claim 5 wherein said evaluation unit is supplied with view data representing a two-dimensional view of said body region obtained with a different examination modality, and wherein said evaluation unit combines said two-dimensional cross-sectional views with said view represented by said view data by overlaying said two-dimensional cross-sectional views with said view represented by said view data based on anatomical landmarks that are present in each of said two-dimensional cross-sectional views and said view represented by said view data.

9. An optical coherence tomography system as claimed in claim 5 wherein said evaluation unit is supplied with view data representing a three-dimensional view of said region obtained by a different examination modality, referenced to said coordinate system, and wherein said evaluation unit combines said three-dimensional view derived from said plurality of two-dimensional cross-sectional views with said three-dimensional view represented by said view data by referencing both of said three-dimensional views to said coordinate system.

* * * * *